AZALEA PLANT
Filed Oct. 22, 1971 2 Sheets-Sheet 1
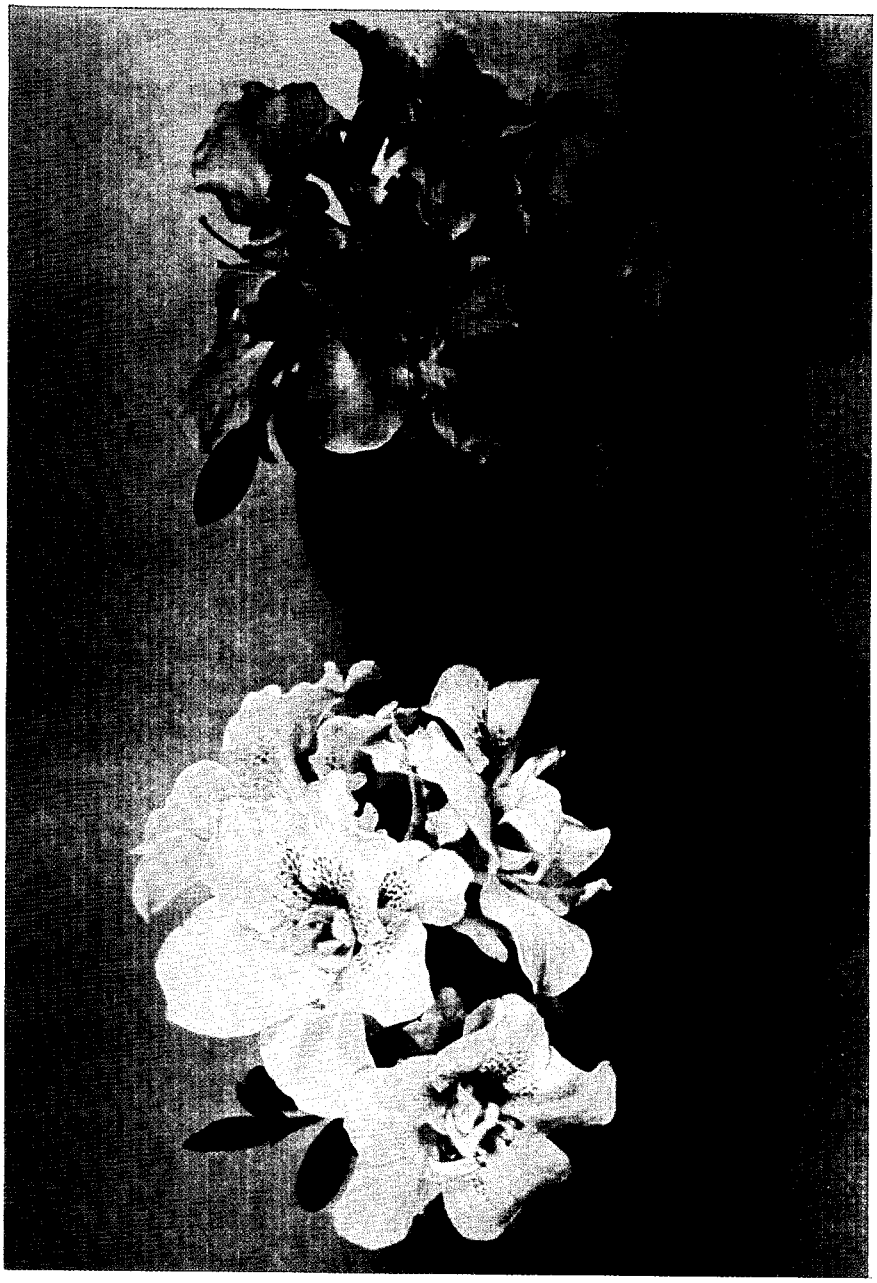

AZALEA PLANT
Filed Oct. 22, 1971 2 Sheets-Sheet 2
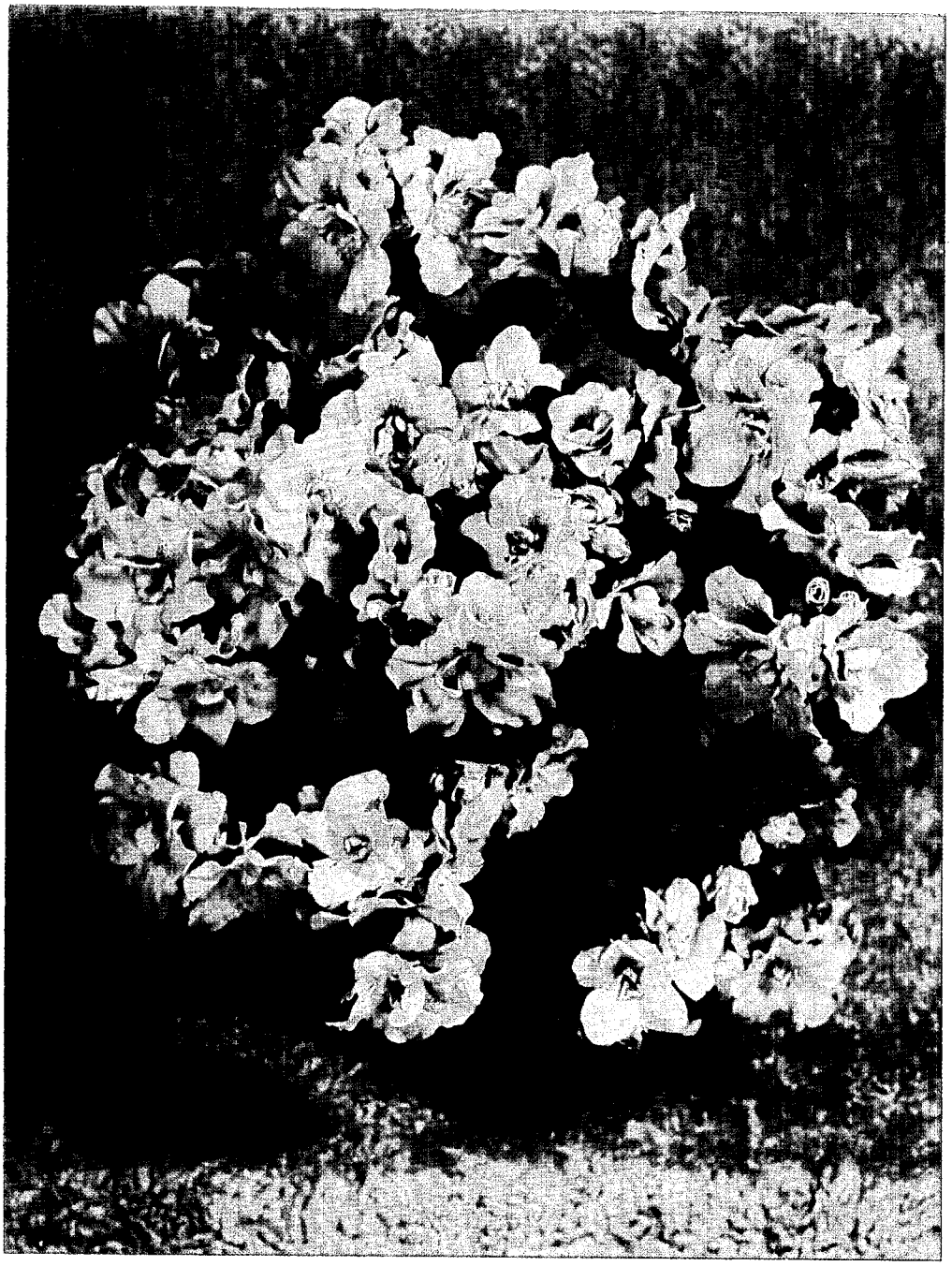

United States Patent Office

Plant Pat. 3,417
Patented Jan. 1, 1974

3,417
AZALEA PLANT

William J. Skou, Akron, Walter W. Knicely, Barberton, and William E. Duffett, Akron, Ohio, assignors to Henry W. Motzkau, Whitewater, Wis.

Filed Oct. 22, 1971, Ser. No. 191,766
Int. Cl. A01h *5/00*
U.S. Cl. Plt.—55 1 Claim

The present invention comprises a new and distinct variety of azalea plant which has resulted from a spontaneous mutation of the unpatented cultivar Skylark.

The new variety is similar in many respects to Skylark, having the same characteristics of:

(1) Growth habit.
(2) Flowering response.
(3) Flower size and form.

The new variety is distinguished from Skylark by its pink and white variegated flower color.

Varietal worth was determined by flowering liners from cuttings taken from the initial selection in both a year-round and natural season developmental flowering program over a period of four years. Stock growth was evaluated in the vicinity of southern Florida.

The new variety has been asexually reproduced by cuttings at Barberton, Ohio, and has been found to retain its distinctive characteristics through successive propagations. When growth in the vicinity of Barberton, Ohio, the new variety has a response described as Earyl-Midseson. The following detailed description is based on observations made of the new variety in a greenhouse in Barberton, Ohio. The response time and blooming period may vary significantly with varying environmental conditions such as temperature, light intensity and day length. Suggested flowering period is from January through April in a natural season program, and all 12 months in a year-round controlled program.

The accompanying photographic drawings show the unique features of the new cultivar, with the colors being as nearly true as possible with color illustrations of this type. Sheet 1 of the drawings comprises a comparison photograph showing flower color and form, with the new cultivar appearing on the left and the parent cultivar, Skylark, on the right. Sheet 2 comprises a specimen photograph of the new cultivar by itself.

The following is a detailed description of our new variety, with color references being to the Munsell Color Book, 1963 Edition, and color comparison made with the parent cultivar Skylark.

Botanical classification: *Rhododendron hybrida* evergreen type; evergreen florist forcing type

| | Skyliner | Skylark |
|---|---|---|
| Flower: | | |
| Color (winter flowering at Barberton Ohio): | | |
| General tonality | Light pink base, nearest to 2.5RP8/6, with an almost white edge, 10P9/1. | Medium pink, nearest to 5RP6/12, but more intense. |
| Sepals first open | Very light pink, lighter than 2.5RP8/6, fading to greenish white, lighter than 2.5GY9/2. | Grayish pink, 7.5RP7/6. |
| Petals unfurl | Light pine, near 2.5RP8/6, with white edge, 10P9/1 | Medium pink, nearest to 5RP6/12, but more intense. |
| Fully open: | | |
| Inside | Light pink, 2.5RP5/6, with white edge, 10P9/1 | Medium pink, lighter than 5RP5/12, but not 5RP6/12. |
| Reverse | do | Do. |
| Base of petals | White, 10P9/1 | Blush, near 10RP9/2. |
| Incomplete outer hose | Light pink, 2.5RP8/6 with white, 10P9/1 | Medium pink, near 5RP5/12, but not as light as 5RP6/12. |
| Variations: | | |
| Dotted uppers | Dark rose pink, nearest to 10RP4/14 | Deep medium pink, near 8.75RP4/14. |
| Discoloration as ages | Gradually fades as ages light pink, much lighter than 2.5RP8/6 | |
| Bud: | | |
| Size | Medium | |
| Form | Conoidal | |
| Opening habit | Petals fully expanded, rose-bud like, fully open, cup-like | |
| Bloom: | | |
| Size | Medium | |
| Average | Range 1½" to 3" | |
| Borne | Several together, average, 3; range, 1 to 6 | |
| Form | Semi-double with varying degrees of petaloid stamen; calyx petaloid to varying degree forming an incomplete hose. | |
| Blooming habit | Once, profusely | |
| Response: | | |
| Natural season | Early to mid season | |
| Year-round | do | |
| Sepals | "Bud Sheath" smooth edge, hairy, persistent | |
| Calyx | Imperfect hose | |
| Length | Medium | |
| Aspect | Hairy | |
| Strength | Strong | |
| Petals: | | |
| Texture | Soft | |
| Appearance | Inside, satiny<br>Outside, satiny | |
| Form | Rounded and slightly notched | |
| Arrangement | Imbricate | |
| Fragrance | None | |
| Persistence | Non-shatter | |
| Longevity | Greenhouse, 3 to 4 weeks<br>Home, 4 to 5 weeks. | |
| Reproductive organs: | | |
| Stamen | Petaloid to varying degrees, 5 to 10 anthers, brownish pink, near 5R6/6. | |
| Filaments | If present, blush pink, 2.5RP9/2; if petaloid, light pink, near 2.5RP8/6. | |
| Style | Normal, columnar, turns upward, pink 7.5RP6/10 | |
| Stigma | Normal, brownish pink, near 5R5/6 | |
| Ovaries | Hypogynous | |
| Fruit | None | |
| Foliage: | | |
| Type | Evergreen | |
| Leaflets | Single | |

Botanical classification: *Rhododendron hybrida* evergreen type; evergreen florist forcing type—continued

| | Skyliner | Skylark |
|---|---|---|
| Size: | | |
| Length | Average 1½", range ⅞ to 2¼" | |
| Width | Average ¾", range ⅜" to 1" | |
| Shape | Ovate | |
| Texture | Slightly hairy | |
| Rib and mid veins | Slightly depressed | |
| Edge | Somewhat repand | |
| Color (new foliage): | | |
| Upper | Green, near 7.5GY5/8 | |
| Lower | Light green, near 5GY6/6 | |
| Color (mature foliage): | | |
| Upper | Darkgreen, near 5GY3/2 | |
| Lower | Gray green, near 7.5GY4/14 | |
| Petiole | Medium length, green, near 5GY5/8 | |
| Plant | Bush | |
| Growth habit | Semi-upright, horizontal | |
| Breaking habit | Vigorous, free breaking, spreading | |
| Size | Average size of a finished product produced from a standard #7 liner by Yoder Brothers, Inc.: height: 10"–12"; diameter: 12"–18". | |
| Rooting habit | Vigorous, on own roots | |
| Budding ease | Fair to good | |
| Uniformity of budding | Good | |
| Growth regulator | Useful in controlling wild growth tendency | |
| Stems (color): | | |
| New wood | Green, near 7.5GY6/10 | |
| Mature wood | Brown, near 10YR4/4 | |
| Responsiveness to day length and temperature: | | |
| Flowering and budding | Buds and flowers under a wide range of environmental conditions | |
| Resistance to cylindrocladium | Good | |
| Cooler tolerance | do | |
| Shipping tolerance | do | |

We claim:

1. A new and distinct variety of azalea characterized particularly as to novelty when compared to the patent cultivar Skylark by its pink and white variegated flower color.

No references cited.

ROBERT E. BAGWILL, Primary Examiner

UNITED STATES PATENT OFFICE
CERTIFICATE OF CORRECTION

Patent No. PP-3,417 Dated January 1, 1974

Inventor(s) WILLIAM J. SKOU, WALTER W. KNICELY and WILLIAM E. DUFFETT

It is certified that error appears in the above-identified patent and that said Letters Patent are hereby corrected as shown below:

Column 2, line 4, change "growth" to --grown--.

In the tabulated description below Columns 1 and 2, under "Flower:", opposite "Petals unfurl", under "Skyliner", change "pine" to --pink--.

In the tabulated description below Columns 1 and 2, directly below "Calyx" and before "Length" insert --Peduncle:-- at the margin.

Signed and sealed this 24th day of September 1974.

(SEAL)
Attest:

McCOY M. GIBSON JR.
Attesting Officer

C. MARSHALL DANN
Commissioner of Patents